United States Patent [19]
Deshayes

[11] Patent Number: 5,342,202
[45] Date of Patent: Aug. 30, 1994

[54] METHOD FOR MODELLING CRANIO-FACIAL ARCHITECTURE

[76] Inventor: Marie-Josèphe Deshayes, 18, rue Pasteur, 14300 Caen (Calvados), France

[21] Appl. No.: 90,654

[22] Filed: Jul. 13, 1993

[51] Int. Cl.$^5$ .................. G09B 23/28; A61C 19/04; A61C 5/00
[52] U.S. Cl. .................................. 434/270; 434/263; 433/68; 433/215
[58] Field of Search .............. 434/263, 270; 433/55, 433/56, 72, 68, 69, 214, 215, 24

[56] References Cited
U.S. PATENT DOCUMENTS

| | | | |
|---|---|---|---|
| 1,706,179 | 3/1929 | McBean | 433/69 |
| 4,528,627 | 7/1985 | Coben | 364/415 |
| 4,631,962 | 12/1986 | Genuit | 73/585 |

*Primary Examiner*—Robert P. Swiatek
*Assistant Examiner*—Cindy A. Cherichetti
*Attorney, Agent, or Firm*—Wolf, Greenfield & Sacks

[57] ABSTRACT

Process for modelling cranio-facial architecture on the basis of a lateral cephalometric X-ray by determining bony points and plotting analysis lines, measuring the angles and comparing them with thresholds and measuring the lengths and comparing the lengths with one another.

5 Claims, 4 Drawing Sheets

METHOD FOR MODELLING CRANIO-FACIAL ARCHITECTURE

The present invention relates to a process for modelling cranio-facial architecture using means established with lateral head X-rays. Bony points are determined and analysis lines are plotted (cephalometrics).

In general, the study of cranio-facial architecture is gaining interest both in medicine and in anthropometry and anthropology. In medicine it concerns in particular dental malocclusions or "orthodontic problems" encountered in children. In the field of anthropology, it concerns the study of the cranio-facial architecture of man and related species.

Various theories have been established for defining standard landmarks and measurements. A more recent analysis (Professor Delaire) consisted of comparing straight lines plotted from bony points with straight lines of an ideal profile. A concept of this type consisting in comparing all the actual measurements (points and angles) with a single ideal model is founded on basically incorrect considerations since this ideal cranium, the point at which all the shapes converge, cannot be used either in medicine or in anthropometry, since each cranium is individual. By means of the process, dental malocclusions in children can be assessed by taking account of the features which are peculiar to the cranium and which differ from those of an ideal cranium defined according to a statistical average. Deshayes' theory consists in identifying the architectural features of the cranium, not by referring to a statistical standard but by recognising the parameters (straight line alignments, angulations, sector proportions) between which there are given relations. There are in effect two architectural growth models, one a flexion model and the other an extension model; within each model, the equilibria can be varied but are always involved in the same biodynamic process. Deshayes proposes a novel process for escaping from the standards conventionally used for comparing measurements. The objective is to find the qualitative value of the measurements in order to classify them within their evolutive model.

The present invention consists of a geometric construction specific to each cranium examined on the basis of a biometric analysis of a lateral cephalometric X-ray.

The object of the present invention is to provide a process for modelling the cranio-facial architecture enabling growth change evolution of the bony points of a cranium to be determined objectively without having to refer to an ideal cranium by applying novel components to the diagram already known from the architectural analysis process of Jean Delaire.

To this end, the invention consists of a geometric construction specific to each cranium examined on the basis of a biometric analysis of a lateral cephalometric X-ray. Bony points are marked on the X-ray; analysis parameters are determined, that is, the discriminating factors of the growth models; a geometric analysis is performed, the straight lines are plotted and the angles and sectors are measured. In total, a geometric structure is produced which takes account of the phenomena encountered within a given growth trajectory.

The modelling system thus described can be performed automatically by a standard computerised method of analysis.

The points are marked by the operator on a numeric digitisation board but are stored and the remainder of the analysis is automatic.

The installation preferably comprises a tracing board with several colours for plotting the straight lines and displaying the results of the analysis.

In accordance with a further variant of the invention, the installation for performing the modelling process consists of a central server, which automatically processes the data provided by remote transmission from local terminals situated at data acquisition locations. In return the central server can transmit the results of the analysis to the terminals. The data collected in this manner can also be used for statistical purposes (database).

The biometric modelling process in accordance with the invention enables individual variations in the craniofacial morphology to be detected and a developing imbalance in young children, which could lead to dental malocclusions, to be traced or even the correction of existing malocclusions to be assessed and their development followed by repeated modelling.

The present invention will be described in detail with reference to the appended drawings in which.

The geometric analysis is performed according to a series of steps of which the chronology characterises the present invention.

Figure 1:
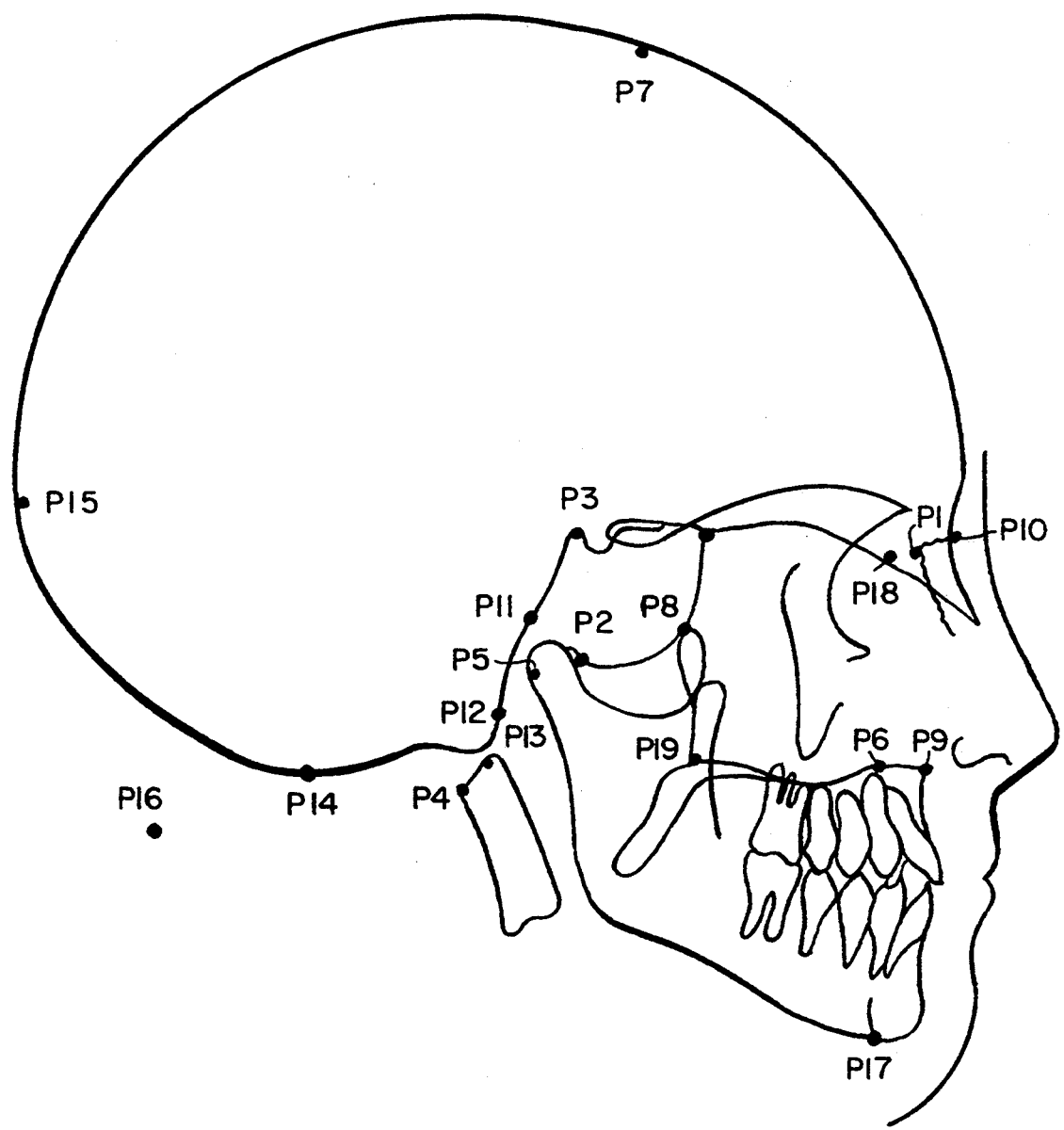
FIG. 1 shows a cranium profile indicating the bony points marked by the operator.

When an X-ray of the cranial profile has been taken, the bony points essential for the analysis are marked on it. These points, which bear the references $P_1$ to $P_{19}$, are conventional and known anatomical reference marks (FIG. 1).

They are defined as follows:
P1: point M—naso fronto maxillary
P2: point CT—temporo condyle
P3: point Clp—upper and posterior clinoid process
P4: point Od—posterior odontoid
P5: point Cp—posterior condyle
P6: point Np—naso palatine
P7: point Br—bregma
P8: point Pts—upper pterygoid
P9: point ENA—anterior nasal spine
P10: point Na—nasion
P11: point SSO—spheno basilar symphysis
P12: Ba—basion
P13: point $O_a$—upper odontoid
P14: point $O_b$—lower occiput
P15: intersection of the cranial contour and the extension of the straight line passing through points P1 and P3;
P16: base of the line taken through the point P15 and perpendicular to the straight line passing through points P1 and P2;
P17: point $M_e$—menton
P18: point $F_M$—maxillo frontal
P19: point $P_{ti}$—posterior nasal spine.

In accordance with the process, the diagram of the straight lines for the analysis is then developed as follows:

1) The straight line D1 passing through points P1 and P2 is plotted;
2) the straight line D2 passing through points P3 and P4 is plotted;
3) the straight line D3 passing through points P1 and P3 is plotted;
4) the angle $\alpha$ between D2 and D3 and the angle $\beta$ between D1 and D3 are measured;
5) point P15 is determined as the intersection between the straight line D3 and the posterior cranial contour;
6) P16 is determined as being the base of the line passing through point P15 and perpendicular to the straight line D1;
7) the sectors P3–P11 and P11–P12 (component of the invention) are plotted;
8) the angle $\overline{P3, P11, P12}$ is compared with 180° (component of the invention);
9) sectors P1–P5 and P16–P5 are compared;
10) the straight line D4 passing through the point P9 and tangential to the cranial contour at point P14 is plotted (component of the invention);
11) the straight line D5 parallel to the straight line D3 passing through P9 is plotted;
12) the angle $\gamma$ between the straight lines D5 and D4 is measured (component of the invention);
13) the location of P19 is marked: below or above D5, P19 is projected onto D5;
14) the location of P13 is marked: below or above D5, P13 is projected onto D5;
15) the straight line D6 originating at P18 and making an angle which is to be calculated in further detail below with the straight line D3 (component of the invention) is plotted;
16) the straight line D8 passing through P18 and P6 is plotted;
17) the angle between the straight lines D8 and D3 is measured;
18) the straight line D7 passing through point P9 and perpendicular to D5 or D4 is plotted according to a process which will be explained in further detail below (component of the invention);
19) P10 is projected orthogonally onto D7: P10' is obtained;
20) P17 is projected orthogonally onto D7: P17' is obtained;
21) the sector P17'–P9 is compared with the ideal sector calculated (component of the invention) which is explained in further detail below.

The components of the invention noted in the process enable the biodynamic growth process to be assessed and the architectural model to be formulated.

In accordance with a particular development of the invention, the cranial discriminants are then determined and the facial geometry analysed.

Figure 2A:
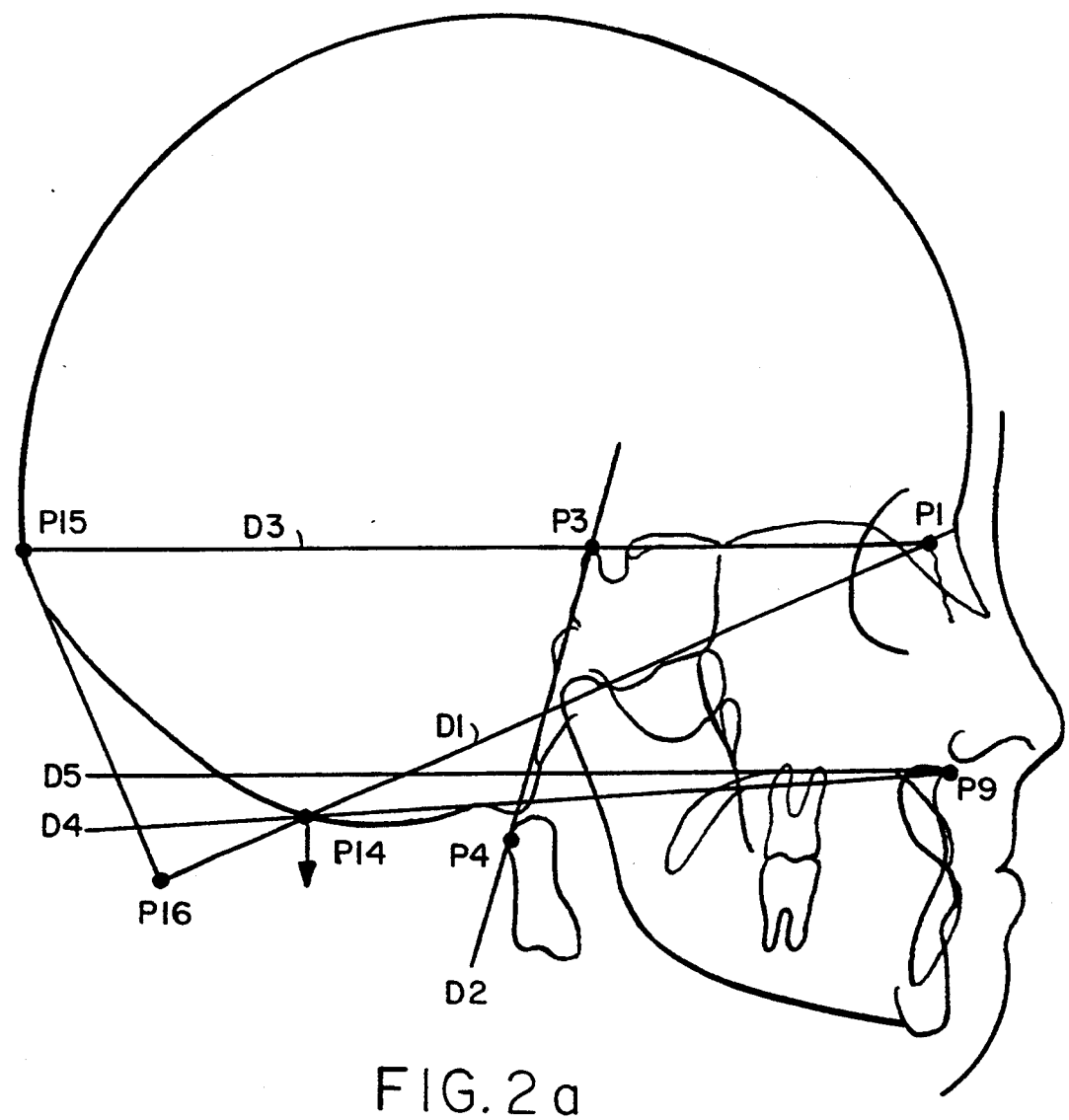
FIGS. 2a and 2b show the diagram of the cranial straight lines in the case of a flexion model.
Figure 2B:
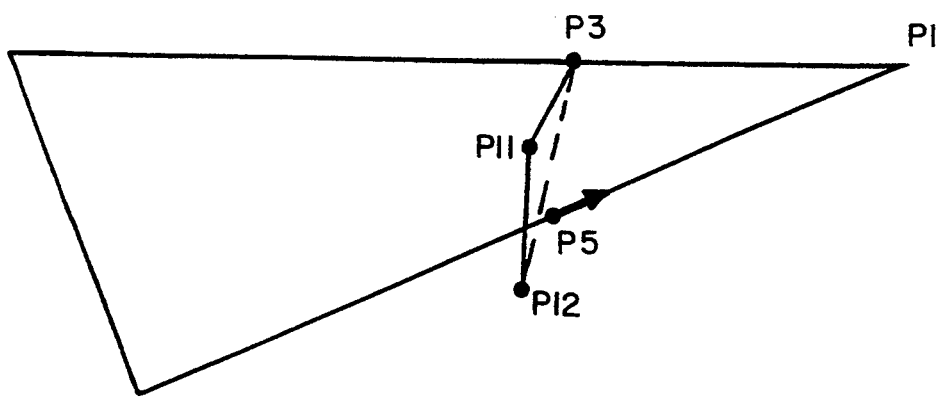
Figure 3A:
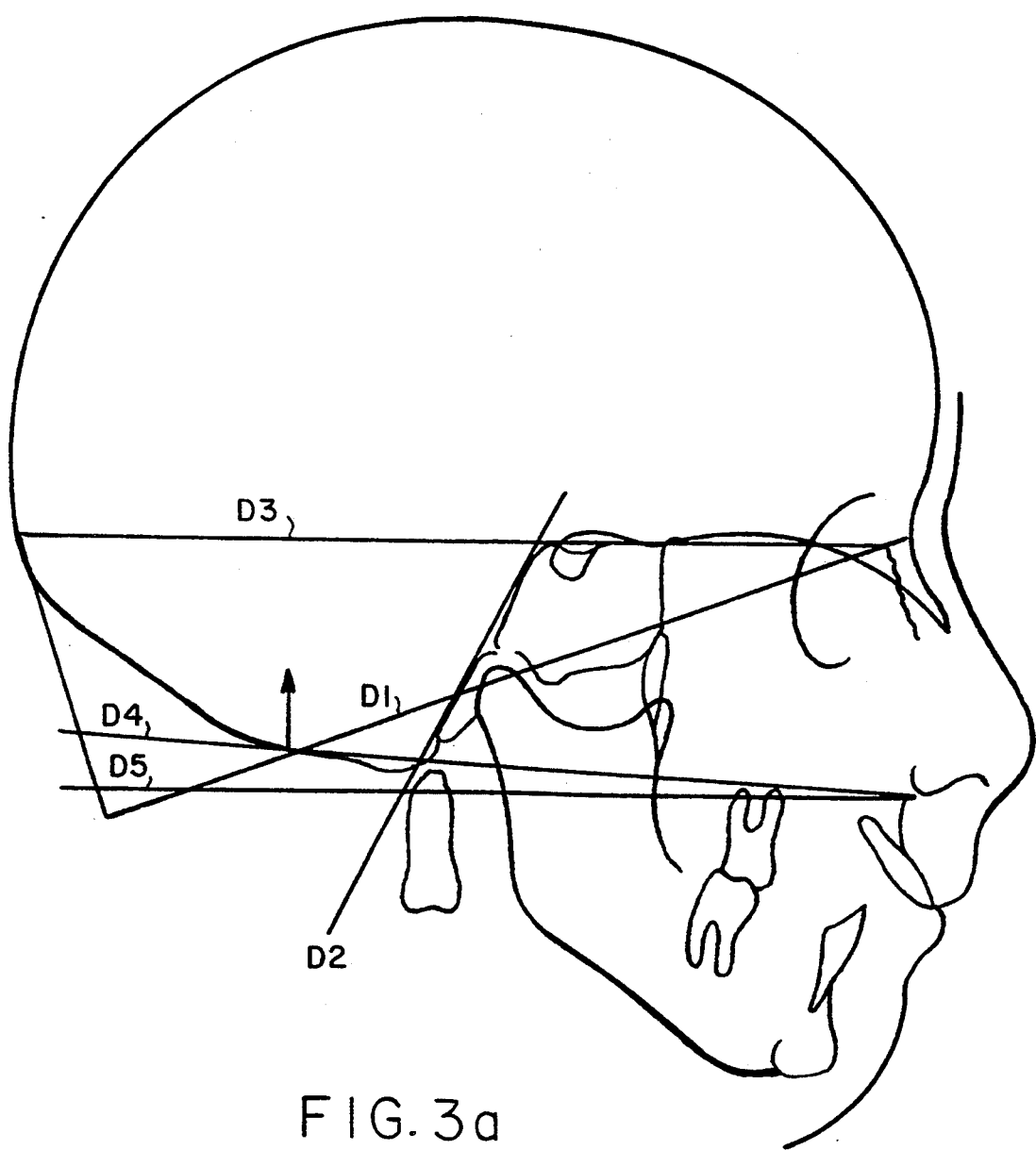
FIGS. 3a and 3b show the diagram of the cranial straight lines in the case of an extension model.
Figure 3B:
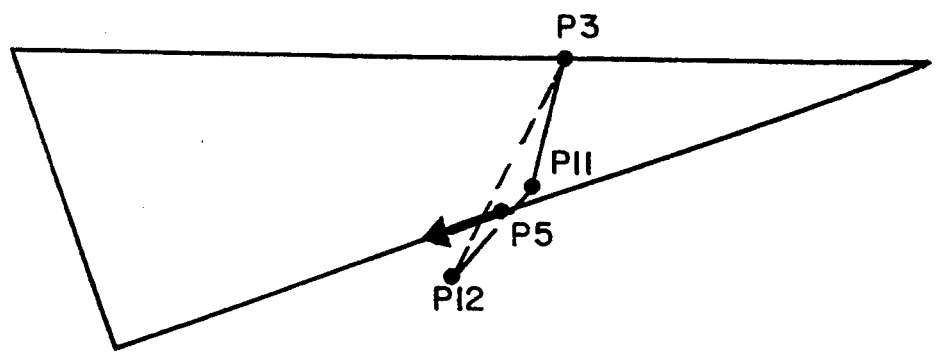

The cranial discriminants of the two growth models are thus determined:

1) the angle $\overline{P3\text{-}P11\text{-}P12}$ is compared with 180° to determine whether this angle is less than or greater than 180°. If it is less than 180°, the model develops as a flexion model (FIG. 2). If it is greater than 180°, it develops as an extension model (FIG. 3).

The flexion model is represented by the point P11 (F) whilst the extension model is represented by the point P11 (E).

2) The length of the sector (P3–P11) is compared with (P11–P12) and (P1–P5) with (P16–P5). It is verified that the following inequalities exist simultaneously:

$$\left.\begin{array}{ll}(P3\text{-}P11) < (P11\text{-}P12) \\ (P1\text{-}P5) < (P16\text{-}P5)\end{array}\right\} - \text{flexion model}$$

or $$\left.\begin{array}{ll}(P3\text{-}P11) > (P11\text{-}P12) \\ (P1\text{-}P5) > (P16\text{-}P5)\end{array}\right\} - \text{extension model}$$

In the first model, the profile is a flexion profile and in the second it is an extension profile.

3) The diagram of the straight lines in FIGS. 2 and 3 is completed by the diagram of the straight lines D4–D5.

The angle $\gamma$ formed between the straight lines D4 and D5 enables the top or bottom location of the occipital scale to be determined qualitatively: by convention:

the algebraic value of the angle $\gamma$ (D5–D4) is negative if P14 is located above D5;

the angle $\gamma$ is positive if P14 is located below D5.

The following stage of the process is the analysis of the facial geometry.

Figure 4:
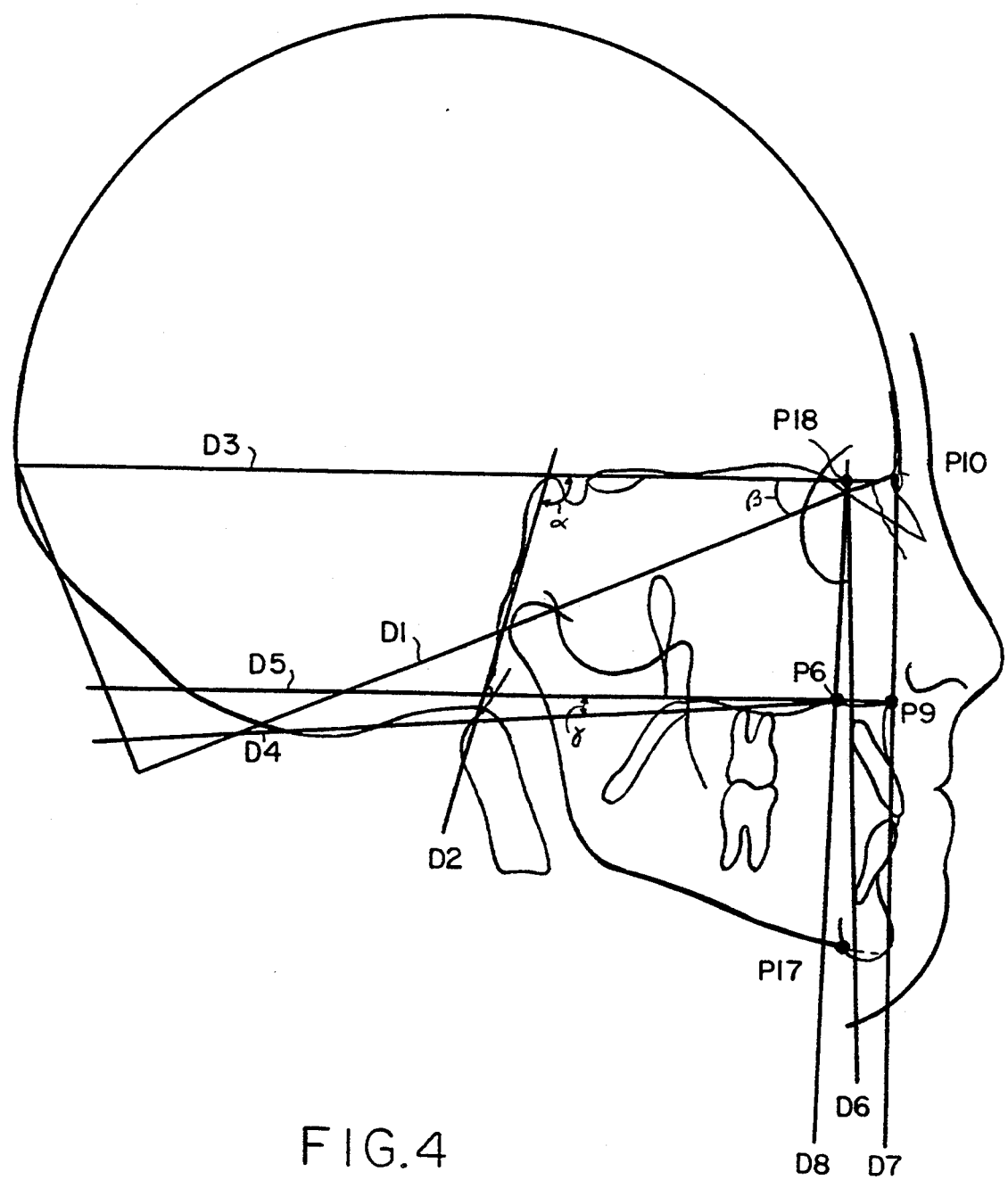
FIG. 4 shows the diagram of the straight lines for the facial analysis.

1) In accordance with FIG. 4, the geometric analysis is completed by the analysis of the facial antero-posterior equilibrium. The facial equilibrium determined by the cranial model is calculated. This equilibrium is materialised by the straight line D6 of which the angle it makes relative to D3, from the point P18, is calculated. This angle is the sum of the two cranial discriminants and a facial discriminant respectively:

the angle $\gamma$ between the straight lines D5–D4 (to be measured);

the angle $\beta$ between the straight lines D1–D3 (to be measured);

the facial tilt angle $\delta$ evaluated statistically to be constant at 65° relative to D1 in Caucasian subjects (this angle varies simply according to ethnic influences).

D6 forms an angle relative to D3 which is equal to the sum of $\gamma + \beta + \delta$. In the example shown in FIG. 4:

$$\left.\begin{array}{ll}\gamma & = 14° \\ \beta & = 23° \\ \delta & = 65°\end{array}\right\} \text{D6 forms an angle of 92° relative to D3}$$

In a further example, if:
$\beta = 20°$
$\gamma = -3°$
the angle between D3 and D6 $= 65° + 20° - 3° = 82°$.

The actual facial tilt is then measured (in the diagram this is the angle D3–D8 in which D8 is marked passing through P6 from P18). The value of the angle between D6 and D3 is compared with the angle D8 – D3:

in the flexion model $\overline{D6/D3} > \overline{D8/D3}$
in the extension model $\overline{D6/D3} < \overline{D8/D3}$ 2) Geometric analysis of the vertical facial equilibrium.

In accordance with a further development of the process according to the invention, the straight line D7 is plotted in order to calculate the ideal vertical equilibrium of the two stages of the face: the upper stage (measured between point P10' and point p9) representing 45% of the total height of the face.

The lower stage from the point p9 is calculated as being 55% and this measurement is compared with the corresponding level of the chin P17'; D7 is traced perpendicular to D5 from P9.

In the flexion model, when the angle $\gamma$ is positive, this theoretical ratio is not modified if the point P19 is located below or on the straight line D5.

If the point P19 is located above the straight line D5, a vertical correction is made to the position of P9: the three points P14, P13 and P19 are projected orthogonally onto D5. The average height is that of P9.

In the extension model, if $\gamma$ is negative, the orientation of the straight line D7 has to be corrected if the absolute value of the angle $\gamma$ is greater than 4°; D7 is no longer plotted perpendicular to D5 from P9 but perpendicular to D4. If the angle $\gamma$ is negative but its absolute value is less than 4°, D7 is plotted perpendicular to D5 and the unmodified position of P9 is preserved.

When the ideal vertical level of the chin is calculated, this measurement is compared with the corresponding level on the actual chin P17':
in the flexion model P17' is below the ideal level;
in the extension model P17' is above the ideal level.

I claim:

1. Process for modelling the cranio-facial architecture from a lateral cephalometric X-ray by determining the bony points and plotting straight lines for analysis, characterised in that a lateral X-ray of the cranium to be analysed is taken and:
the following points P1, P2, P3 ... P16, P17, P18, P19 are determined on the X-ray;
the straight line D1 passing through points P1, P2, the straight line D2 passing through points P3, P4, and the straight line D3 passing through points P1, P3 are plotted;
point P15 is determined as the intersection between the straight line D3 and the posterior cranial contour;
point P16 is determined as the base of the line taken through the point P15 and perpendicular to the straight line D1;
the angle $\widehat{(P3, P11, P12)}$ is compared with 180°;
the sectors $\widehat{(P3, P11)}$ and $\widehat{(P11, P12)}$ are compared;
the sectors $\widehat{(P1, P5)}$ and $\widehat{(P16, P5)}$ are compared;
the straight line D4 passing through point P9 and tangential to the cranial contour at point P14 is plotted;
the straight line D5 parallel with the straight line D3 passing through point P9 is plotted;
the angle $\gamma$ between the straight lines (D5, D4) is measured;
the algebraic sign (positive or negative) of the angle $\gamma$ is determined;
the diagram is classified as a cranial flexion model if $\widehat{(P3, P11, P12)} < 180°$ $\widehat{(P3, P11)} < \widehat{(P11, P12)}$ $\widehat{(P1, P5)} < \widehat{(P16, P5)}$ $\gamma$ positive
and is a cranial extension model if $\widehat{(P3, P11, P12)} > 180°$ $\widehat{(P3, P11)} > \widehat{(P11, P12)}$ $\widehat{(P1, P5)} > \widehat{(P16, P5)}$ $\gamma$ negative
the above points being defined as follows:

P1: point M—naso fronto maxillary
P2: point CT—temporo condyle
P3: point Clp—upper and posterior clinoid process
P4: point Od—posterior odontoid
P5: point Cp—posterior condyle
P6: point Np—naso palatine
P7: point Br—bregma
P8: point Pts—upper pterygoid
P9: point ENA—anterior nasal spine
P10: point Na—nasion
P11: point SSO—spheno basilar symphysis
P12: Ba—basion
P13: point $O_a$—upper odontoid
P14: point $O_b$—lower occiput
P15: intersection of the cranial contour and the extension of the straight line passing through points P1 and P3;
P16: base of the line taken through point P15 and perpendicular to the straight line passing through points P1 and P2;
P17: point $M_e$—menton
P18: point $F_M$—maxillo frontal
P19: point $P_{ti}$—posterior nasal spine.

2. Process according to claim 1, characterised in that:
the angle $\beta$ is measured=(D1, D3);
the angle $\delta = 65°$ is taken as the constant angle;
the angle $\gamma$ is measured=(D5, D4);
the sum of angles $\beta$, $\delta$, $\gamma$ is calculated;
the straight line D6 originating at P18 and forming angle $\beta + \gamma + \delta$ with the straight line D3 is plotted.

3. Process according to claim 2, characterised in that:
the straight line D8 passing through P18 and P6 is plotted;
the angles $\widehat{D6\,D3}$ and $\widehat{D8\,D3}$ are compared;
it is concluded that there is facial flexion if $\widehat{D6\,D3} > \widehat{D8\,D3}$;
it concluded that there is facial extension if $\widehat{D6\,D3} < \widehat{D8\,D3}$.

4. Process according to claim 2, characterised in that:
the straight line D7 passing through P9 and perpendicular to D5 or D4 is plotted depending on whether
$\gamma < -4°$ when D7 is perpendicular to D4
$\gamma > -4°$ when D7 is perpendicular to D5.

5. Process according to one of claims 2 to 4, characterised in that:
the straight line D7 is plotted to calculate the ideal vertical equilibrium of the two stages of the face: the upper stage (measured between point P10' and point P9) representing 45° of the total height of the face;
the lower stage from point P9 is calculated as being 55% and this measurement is compared with the corresponding level of the chin P17' (P17 projected onto the straight line D7), D7 being plotted perpendicular to D5 from P9;
if the facial model is a flexion model, when the angle $\gamma$ is positive, this theoretical ratio is not modified if point P9 is located below or on the straight line D5, however, if point P19 is located above the straight line D5, a vertical correction of the position of P9 is made: the three points P14, P13 and P19 are projected orthogonally onto D5, the average height being that of P9;
when the ideal vertical level on the chin is calculated, this measurement is compared with the corresponding level on the actual chin P17': and it is concluded that:
there is facial flexion if P17' is below the ideal level;
there is facial extension if P17' is above the ideal level.

* * * * *